United States Patent
Veldman

(10) Patent No.: US 10,185,303 B2
(45) Date of Patent: Jan. 22, 2019

(54) OPTIMIZING COMPUTATIONAL EFFICIENCY BY MULTIPLE TRUNCATION OF SPATIAL HARMONICS

(71) Applicant: KLA-Tencor Corporation, Milpitas, CA (US)

(72) Inventor: Andrei Veldman, Sunnyvale, CA (US)

(73) Assignee: KLA-Tencor Corporation, Milpitas, CA (US)

(*) Notice: Subject to any disclaimer, the term of this patent is extended or adjusted under 35 U.S.C. 154(b) by 245 days.

(21) Appl. No.: 15/048,981

(22) Filed: Feb. 19, 2016

(65) Prior Publication Data

US 2016/0246285 A1   Aug. 25, 2016

Related U.S. Application Data

(60) Provisional application No. 62/119,175, filed on Feb. 21, 2015.

(51) Int. Cl.
| | | |
|---|---|---|
| *G01N 21/25* | (2006.01) | |
| *G05B 19/406* | (2006.01) | |

(Continued)

(52) U.S. Cl.
CPC ........ *G05B 19/406* (2013.01); *G01B 11/0641* (2013.01); *G01N 21/211* (2013.01);
(Continued)

(58) Field of Classification Search
None
See application file for complete search history.

(56) References Cited

U.S. PATENT DOCUMENTS

| | | |
|---|---|---|
| 5,608,526 A | 3/1997 | Piwonka-Corle et al. |
| 5,859,424 A | 1/1999 | Norton et al. |

(Continued)

FOREIGN PATENT DOCUMENTS

WO   2014139855 A1   9/2014

OTHER PUBLICATIONS

International Search Report dated May 30, 2016, for PCT Application No. PCT/US2016/018985 filed on Feb. 22, 2016 by KLA-Tencor Corporation, 3 pages.

*Primary Examiner* — Michael Lebentritt
(74) *Attorney, Agent, or Firm* — Spano Law Group; Joseph S. Spano

(57) ABSTRACT

Methods and systems for solving measurement models of complex device structures with reduced computational effort and memory requirements are presented. The computational efficiency of electromagnetic simulation algorithms based on truncated spatial harmonic series is improved for periodic targets that exhibit a fundamental spatial period and one or more approximate periods that are integer fractions of the fundamental spatial period. Spatial harmonics are classified according to each distinct period of the target exhibiting multiple periodicity. A distinct truncation order is selected for each group of spatial harmonics. This approach produces optimal, sparse truncation order sampling patterns, and ensures that only harmonics with significant contributions to the approximation of the target are selected for computation. Metrology systems employing these techniques are configured to measure process parameters and structural and material characteristics associated with different semiconductor fabrication processes.

20 Claims, 14 Drawing Sheets

(51) Int. Cl.
  *G01N 21/21*      (2006.01)
  *G01B 11/06*      (2006.01)
  *G03F 7/20*       (2006.01)

(52) U.S. Cl.
  CPC ........... *G01N 21/255* (2013.01); *G03F 7/705* (2013.01); *G03F 7/70625* (2013.01); *G03F 7/70633* (2013.01); *G01B 2210/56* (2013.01); *G01N 2021/213* (2013.01); *G01N 2201/061* (2013.01); *G01N 2201/0683* (2013.01); *G01N 2201/12* (2013.01); *G05B 2219/45031* (2013.01)

(56) References Cited

U.S. PATENT DOCUMENTS

| | | | |
|---|---|---|---|
| 5,959,726 A * | 9/1999 | Riley | G01M 11/0292 356/124.5 |
| 6,429,943 B1 | 8/2002 | Opsal et al. | |
| 6,633,831 B2 | 10/2003 | Nikoonahad et al. | |
| 6,734,967 B1 | 5/2004 | Piwonka-Corle et al. | |
| 6,816,570 B2 | 10/2004 | Janik et al. | |
| 6,876,443 B2 * | 4/2005 | Barth | G01M 11/0292 348/E17.002 |
| 6,895,075 B2 | 5/2005 | Yokhin et al. | |
| 6,972,852 B2 | 12/2005 | Opsal et al. | |
| 7,075,633 B2 * | 7/2006 | Wegmann | G01M 11/0285 250/201.9 |
| 7,330,609 B2 * | 2/2008 | Wang | G01M 11/0292 250/370.09 |
| 7,405,816 B2 * | 7/2008 | Ojanen | H04N 17/002 348/187 |
| 7,428,060 B2 | 9/2008 | Jin et al. | |
| 7,450,225 B1 | 11/2008 | Liu et al. | |
| 7,478,019 B2 | 1/2009 | Zangooie et al. | |
| 7,649,682 B2 * | 1/2010 | Olschewski | G02B 21/365 359/363 |
| 7,698,098 B2 | 4/2010 | Ritter et al. | |
| 7,826,071 B2 | 11/2010 | Shchegrov et al. | |
| 7,879,515 B2 * | 2/2011 | Ausschnitt | G03F 7/70633 257/797 |
| 7,921,383 B1 | 4/2011 | Wei | |
| 7,929,667 B1 | 4/2011 | Zhuang et al. | |
| 7,933,026 B2 | 4/2011 | Opsal et al. | |
| 8,214,771 B2 | 7/2012 | Adel et al. | |
| 8,250,497 B2 * | 8/2012 | Hsu | G03F 7/70633 356/399 |
| 8,289,527 B2 | 10/2012 | Li et al. | |
| 8,296,687 B2 | 10/2012 | Mitrovic et al. | |
| 8,440,475 B2 * | 5/2013 | Habets | G03F 7/705 324/500 |
| 9,395,633 B2 * | 7/2016 | Danilin | G03F 7/70516 |
| 9,470,639 B1 * | 10/2016 | Zhuang | G01N 21/9501 |
| 9,714,827 B2 * | 7/2017 | Van Der Schaar | G01B 11/27 |
| 2003/0160163 A1 * | 8/2003 | Wong | G02B 27/46 250/237 R |
| 2003/0187604 A1 | 10/2003 | Drege et al. | |
| 2004/0207849 A1 * | 10/2004 | Nikoonahad | G03F 7/70633 356/401 |
| 2007/0223011 A1 | 9/2007 | Jin et al. | |
| 2008/0049214 A1 | 2/2008 | Maznev et al. | |
| 2010/0042388 A1 * | 2/2010 | Bischoff | G06E 1/00 703/6 |
| 2010/0177324 A1 | 7/2010 | Walsh et al. | |
| 2010/0274521 A1 | 10/2010 | Rabello et al. | |
| 2011/0288822 A1 * | 11/2011 | Veldman | G02B 5/1847 702/189 |
| 2012/0323356 A1 | 12/2012 | Dziura et al. | |
| 2013/0114085 A1 | 5/2013 | Wang et al. | |
| 2013/0116978 A1 | 5/2013 | Yoo et al. | |
| 2014/0111791 A1 | 4/2014 | Manassen et al. | |
| 2014/0172394 A1 | 6/2014 | Kuznetsov et al. | |
| 2014/0222380 A1 | 8/2014 | Kuznetsov et al. | |
| 2014/0297211 A1 | 10/2014 | Pandev et al. | |
| 2014/0316730 A1 | 10/2014 | Shchegrov et al. | |
| 2014/0358476 A1 * | 12/2014 | Backues | G01N 21/211 702/167 |
| 2015/0042984 A1 | 2/2015 | Pandev et al. | |
| 2015/0046118 A1 | 2/2015 | Pandev et al. | |
| 2015/0198524 A1 * | 7/2015 | Sapiens | G02B 27/56 356/445 |
| 2015/0233818 A1 * | 8/2015 | Manassen | G01N 21/41 356/369 |
| 2016/0061750 A1 * | 3/2016 | Den Boef | G01B 11/00 355/67 |
| 2016/0266505 A1 * | 9/2016 | Amit | H01L 22/12 |
| 2017/0307983 A1 * | 10/2017 | Den Boef | G03F 7/70133 |

* cited by examiner

| RATIO OF LARGE PITCH TO SMALL PITCH | INCREASE IN COMPUTATIONAL COST |
|---|---|
| 2:1 | 8X |
| 3:1 | 27X |
| 4:1 | 64X |
| 5:1 | 125X |
| 8:1 | 512X |
| 10:1 | 1000X |
| 4:1 IN X-DIR 2:1 IN Y-DIR | 512X |

OPTIMIZING COMPUTATIONAL EFFICIENCY BY MULTIPLE TRUNCATION OF SPATIAL HARMONICS

CROSS REFERENCE TO RELATED APPLICATION

The present application for patent claims priority under 35 U.S.C. § 119 from U.S. provisional patent application Ser. No. 62/119,175, entitled "Method for Optimizing Computational Efficiency by Multiple Truncation of Spatial Harmonics," filed Feb. 21, 2015, the subject matter of which is incorporated herein by reference in its entirety.

TECHNICAL FIELD

The described embodiments relate to metrology systems and methods, and more particularly to methods and systems for measurement of multiple periodic metrology targets with reduced computational effort.

BACKGROUND INFORMATION

Semiconductor devices such as logic and memory devices are typically fabricated by a sequence of processing steps applied to a specimen. The various features and multiple structural levels of the semiconductor devices are formed by these processing steps. For example, lithography among others is one semiconductor fabrication process that involves generating a pattern on a semiconductor wafer. Additional examples of semiconductor fabrication processes include, but are not limited to, chemical-mechanical polishing, etch, deposition, and ion implantation. Multiple semiconductor devices may be fabricated on a single semiconductor wafer and then separated into individual semiconductor devices.

Optical metrology processes are used at various steps during a semiconductor manufacturing process to detect defects on wafers to promote higher yield. Optical metrology techniques offer the potential for high throughput without the risk of sample destruction. A number of optical metrology based techniques including scatterometry and reflectometry implementations and associated analysis algorithms are commonly used to characterize critical dimensions, overlay, film thicknesses, process parameters, composition and other parameters of nanoscale structures.

As devices (e.g., logic and memory devices) move toward smaller nanometer-scale dimensions, characterization becomes more difficult. Devices incorporating complex three-dimensional geometry and materials with diverse physical properties contribute to characterization difficulty.

In response to these challenges, more complex optical tools have been developed. Measurements are performed over a large ranges of several machine parameters (e.g., wavelength, azimuth and angle of incidence, etc.), and often simultaneously. As a result, the measurement time, computation time, and the overall time to generate reliable results, including measurement recipes, increases significantly.

Existing model based metrology methods typically include a series of steps to model and then measure structure parameters. Typically, measurement data (e.g., measured data, DOE data, etc.) is collected from a particular metrology target. An accurate measurement model of the optical system, dispersion parameters, and geometric features is formulated. An electromagnetic (EM) solver is employed to solve the measurement model and predict measurement results. A series of simulations, analysis, and regressions are performed to refine the measurement model and determine which model parameters to float. In some examples, a library of synthetic spectra is generated. Finally, measurements are performed using the library or regression in real time with the measurement model.

The EM simulation process is controlled by a number of parameters (e.g., slabbing parameters, Rigorous Coupled Wave Analysis (RCWA) parameters, discretization parameters, etc.). Simulation parameters are selected to avoid introducing excessively large errors. However, in general, there is a trade-off between computational effort and solution accuracy. In other words, an accurate solution requires much more computational effort than a less accurate solution. Currently, the computational effort required to arrive at sufficiently accurate measurement results for complex semiconductor structures is large and growing larger.

Many EM simulation algorithms are based on spatial Fourier harmonic expansions of the dielectric permittivity of a target and of the electric and magnetic fields incident and scattered by the target. These algorithms are widely used in semiconductor metrology due to their stability, and ability to achieve the desired accuracy with relatively high speed. Exemplary algorithms include Rigorous Coupled Wave Analysis (RCWA), Classical Modal Method, Finite Difference methods, etc. These algorithms are typically employed to compute electromagnetic scattering by periodic targets. The algorithms use Fourier expansions of the periodic targets and the electromagnetic fields in terms of spatial harmonics. In principle, Fourier series expansions have an infinite number of terms. However, in practical computations by digital computers, a truncated version of the Fourier series expansion having a finite number of Fourier harmonics in a range between a minimum and a maximum spatial frequency are employed. The truncation order (TO) of the Fourier series expansion is commonly identified as the highest order spatial harmonic of the truncated Fourier expansion.

Many current metrology systems employ a RCWA algorithm as the EM simulation engine employed to solve the measurement model. Simulated measurement signals are computed by the RCWA engine. In some embodiments, measured signals are compared to the computed signals as part of a regression analysis to estimate measurement parameter values.

To simulate measurement signals generated by a periodic metrology target using RCWA, the profiles of periodic structures are approximated by a number of sufficiently thin planar grating slabs. RCWA involves three main steps: 1) Fourier expansion of the electric and magnetic fields inside the grating, 2) Solution of Maxwell's equations by calculation of the eigenvalues and eigenvectors of a constant coefficient matrix that characterizes the diffracted signal, or an equivalent method, and 3) Solution of a linear system deduced from the boundary matching conditions. The analysis is divided into three distinct spatial regions: 1) the ambient region supporting the incident plane wave field and a summation over all reflected diffracted orders, 2) the grating structure and underlying non-patterned layers where the wave field is treated as a superposition of modes associated with each diffracted order, and 3) the substrate containing the transmitted wave field.

The accuracy of the RCWA solution depends, in part, on the number of terms retained in the space-harmonic expansion of the wave fields. The number of terms retained is a function of the number of spatial harmonic orders considered during the calculations. Efficient generation of a simulated diffraction signal for a given hypothetical profile involves selection of the optimal set of spatial harmonics orders at each wavelength for transverse-magnetic (TM) components of the diffraction signal, transverse-electric (TE) components of the diffraction signal, or both. Mathematically, the more spatial harmonic orders selected, the more accurate the simulations. However, this comes at a price of higher computational effort and memory consumption. Moreover, the computational effort and memory consumption is a strongly nonlinear function of the number of orders used. Typically, computational effort scales with the third power for simulations of two dimensional structures and scales with the sixth power for three dimensional structures. Similarly, memory consumption scales with the second power for two dimensional structures and to the fourth power for three dimensional structures.

The importance of selecting the appropriate number of spatial harmonic orders increases significantly when three-dimensional structures are considered in comparison to two-dimensional structures. Since the selection of the number of spatial harmonic orders is application specific, efficient approaches for selecting the number of spatial harmonics orders can be critical to achieve sufficiently accurate results in a reasonable period of time.

In some examples, a compact pattern of spatial harmonics is selected. In these examples a single truncation order (TO) is selected in each direction of periodicity of the target, and all Fourier harmonics within the range of the selected TO are typically used. For example, if the target is periodic in one direction (e.g., a two dimensional line-space grating, etc.), a single TO is determined by trading off computation time for simulation accuracy, and all of the spatial harmonics in the range $\{-TO, +TO\}$ are employed. If the target is periodic in two directions (e.g., an array of contact holes, two crossed-gratings, etc.), then a TO associated with each direction (e.g., $TO_x$ and $TO_y$) is selected in a similar manner. Similarly, all of the spatial harmonics in the rectangular region with corners $(-TO_x, -TO_y)$, $(+TO_x, -TO_y)$, $(+TO_x, +TO_y)$, and $(-TO_x, +TO_y)$ are employed in the simulation.

In some examples, a sparse pattern of spatial harmonics is selected. U.S. Patent Publication No. 2011/0288822 A1 by Veldman et al. and U.S. Pat. No. 7,428,060 B2 to Jin et al., incorporated herein by reference in their entirety, describe the selection of non-rectangular patterns of Fourier modes for three dimensional grating structures based on the convergence of the computation algorithm.

However, these approaches to selecting the pattern of spatial harmonics become problematic when the periodic structure has two or more characteristic repeating length scales in one or more directions of periodicity, particularly when one or more of the repeating length scales is relatively large. In these approaches, a large period requires a large truncation order, even if the other repeating length scales are relatively small. Hence, in these approaches, the TO is dictated by the largest pitch.

When current systems are employed to measure complex geometric structures, three dimensional structures, and structures having multiple periods in each direction, a high truncation order is necessary to accurately represent the corresponding physical measurement signals. This significantly increases the required computational effort. In some examples, when faced with multiple pediodicity, EM simulation algorithms commonly used in metrology can be slowed by several orders of magnitude relative to single-period structures.

To meet the increasing computational burden, large computing clusters are required, and in some cases it is impractical to perform the necessary computations for some models. Although a lower truncation order may be employed to reduce the required computational effort, this often results in unacceptably large measurement errors.

Increasingly complicated measurement models are causing corresponding increases in computational effort. Improved model solution methods and tools are desired to arrive at sufficiently accurate measurement results with reduced computational effort.

SUMMARY

Methods and systems for solving measurement models of complex device structures with reduced computational effort and memory requirements are presented. The computational efficiency of electromagnetic simulation algorithms based on truncated spatial harmonic series is improved for periodic targets that exhibit a fundamental spatial period and one or more approximate periods that are integer fractions of the fundamental spatial period.

In one aspect, Fourier spatial harmonics are grouped based on the multiple periodicity of the metrology target. The Fourier spatial harmonics associated with each distinct period of the target are grouped separately. A distinct truncation order and a distinct spacing between selected harmonics are selected for each group. This approach produces optimal, sparse truncation order sampling patterns, and ensures that only harmonics with significant contributions to the approximation of the target are selected for computation. Furthermore, the computational effort associated with grouping and selecting harmonics in the manner described herein is minimal compared to existing approaches.

The selected harmonics are subsequently used for regression, library generation, or other analyses where simulated model based measurement signals are typically employed as part of an effort to characterize structural, material, and process parameters in semiconductor manufacturing.

In a further aspect, the classification of spatial harmonics into groups with separate truncation orders is implemented in each direction of the metrology target that exhibits multiple periodicities.

In another further aspect, the methods and systems described herein are applied to EM algorithms that approximate finite target effects by assuming a periodic target with a small period divided into patches having a much larger period. In this manner a finite target is analyzed by dividing the target grating into periodic patches.

Metrology systems employing these techniques are configured to measure process parameters and structural and material characteristics (e.g., material composition, dimensional characteristics of structures and films, etc.) associated with different semiconductor fabrication processes.

The foregoing is a summary and thus contains, by necessity, simplifications, generalizations and omissions of detail; consequently, those skilled in the art will appreciate that the summary is illustrative only and is not limiting in any way. Other aspects, inventive features, and advantages of the devices and/or processes described herein will become apparent in the non-limiting detailed description set forth herein.

DETAILED DESCRIPTION

Reference will now be made in detail to background examples and some embodiments of the invention, examples of which are illustrated in the accompanying drawings.

Methods and systems for solving measurement models of complex device structures with reduced computational effort are presented. More specifically, the computational efficiency of electro-magnetic (EM) simulation algorithms based on truncated spatial harmonic series is improved when the periodic target exhibits multiple periodicities. As described herein, a periodic target having multiple periods includes a fundamental spatial period, and one or more approximate periods that are integer fractions of the fundamental spatial period. Metrology systems employing these techniques are configured to measure process parameters and structural and material characteristics (e.g., material composition, dimensional characteristics of structures and films, etc.) associated with different semiconductor fabrication processes.

Figure 1A:
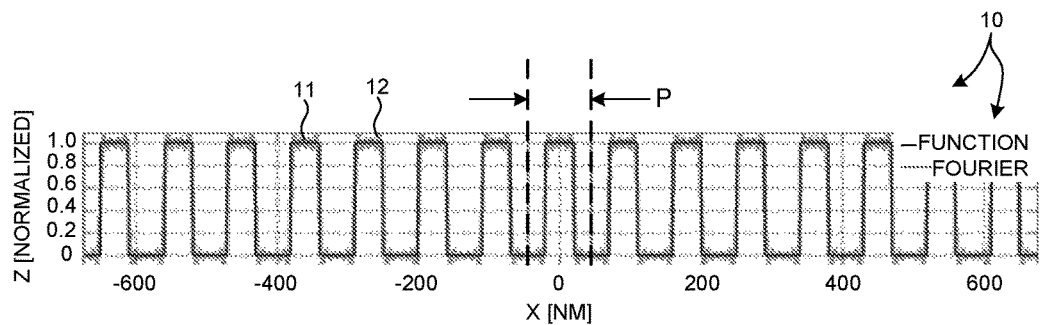
FIG. 1A depicts a plot 10 illustrative of a periodic target function 11 and a Fourier series approximation 12 of the periodic target function 11.

FIG. 1A depicts a plot 10 illustrative of a periodic target function 11 having a spatial period, P, in the x-direction. Mathematically, the periodicity condition is f(x)=f(x+P), for all values of x. In this example, P, is the distance that satisfies the periodicity condition.

In Fourier space, the periodic target function 11 can be expanded into a discrete Fourier series having equally spaced harmonics. The Fourier series expansion is described in equation (1), where n is the order number, x is the position in the x-direction, and P is the selected fundamental period of the Fourier series expansion.

$$f(x) = \sum_{-\infty}^{\infty} A_n e^{i\frac{2\pi n x}{P}} \quad (1)$$

The coefficients of the expansion, $A_n$, are described in equation (2).

$$A_n = \frac{1}{P} \int_0^P f(x) e^{-i\frac{2\pi n x}{P}} dx \quad (2)$$

As described in equations (1) and (2), the Fourier series expansion has, in general, an infinite number of harmonic terms. However, in practical computations on digital computers only a finite number of Fourier harmonics are used. Thus, the Fourier series expansion must be truncated to a finite number of harmonic terms. The maximum order of the harmonics used in a truncated Fourier expansion is called the Truncation Order (TO), and the spatial harmonics within the range between the minimum and maximum spatial frequency are employed. Equation (3) describes a Fourier series expansion truncated at TO.

$$f(x) = \sum_{n=-TO}^{TO} A_n e^{i\frac{2\pi n x}{P}} \quad (3)$$

The spacing between adjacent Fourier harmonics in reciprocal space (i.e., k-space) is $$HarmonicSpacing = \frac{2\pi}{P} \quad (4)$$

Figure 1B:
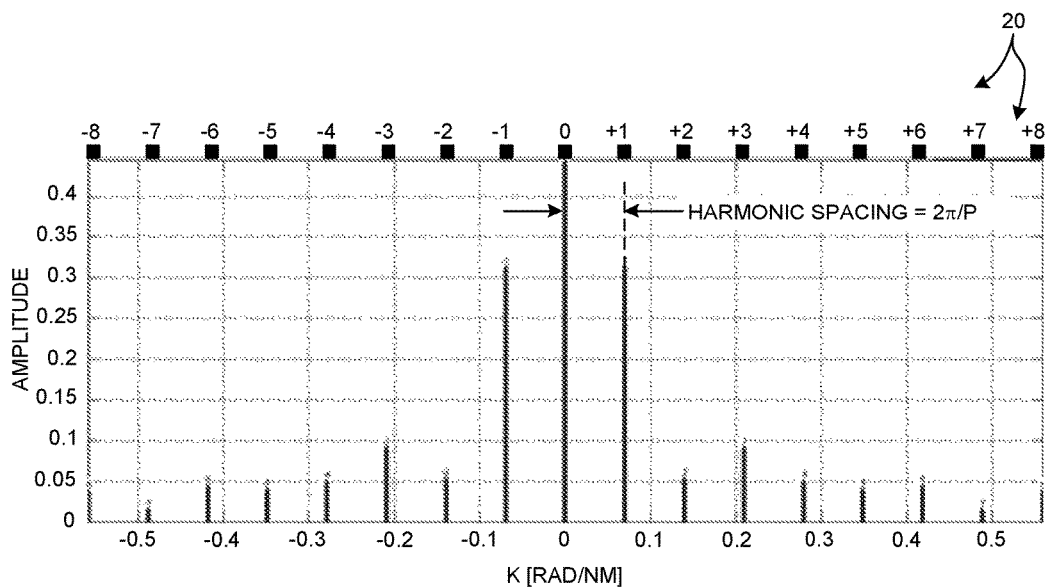
FIG. 1B depicts a plot 20 illustrative of the amplitude of the spatial harmonics comprising the Fourier series approximation 12.
Figure 1C:
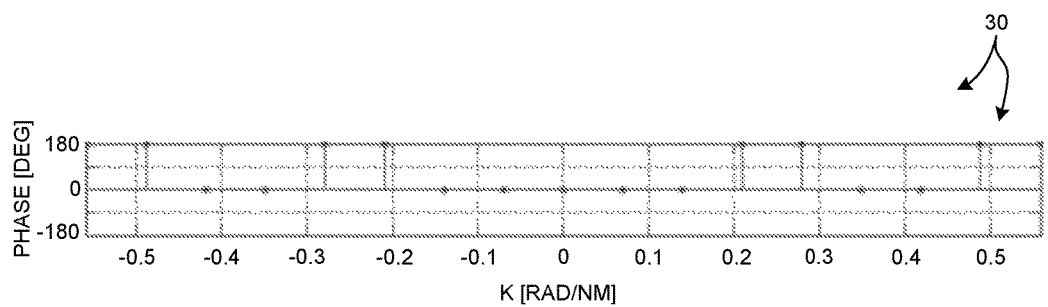
FIG. 1C depicts a plot 30 illustrative of the phase of the spatial harmonics comprising the Fourier series approximation 12.

FIG. 1A also illustrates a Fourier series approximation 12 of the periodic target function 11. FIG. 1B depicts a plot 20 illustrative of the amplitude of the spatial harmonics comprising the Fourier series approximation up to the selected truncation order value, TO=8. FIG. 1C depicts a plot 30 illustrative of the phase of the spatial harmonics comprising the Fourier series approximation up to the selected truncation order value. As depicted in FIG. 1B, the harmonic spacing in k-space is equal to $2\pi/P$.

Figure 2A:
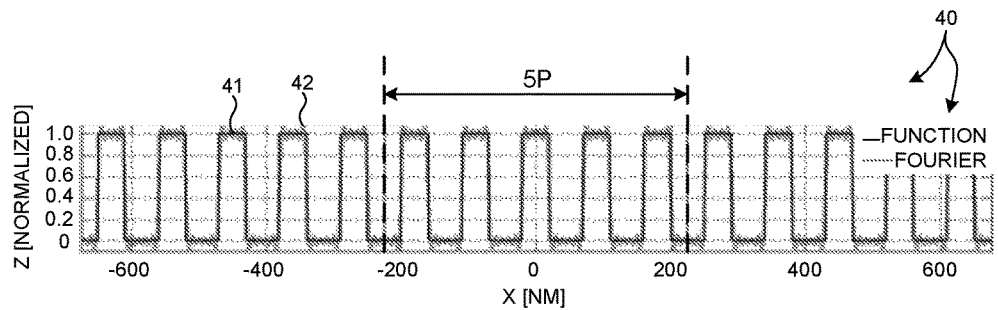
FIG. 2A depicts a plot 40 illustrative of a periodic target function 41 and a Fourier series approximation 42 of the periodic target function 41.
Figure 2B:
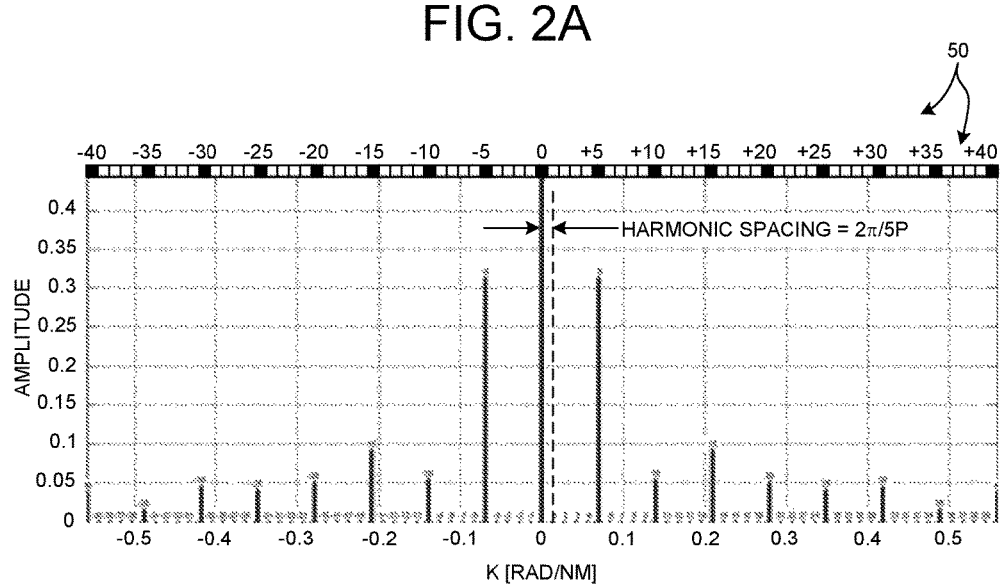
FIG. 2B depicts a plot 50 illustrative of the amplitude of the spatial harmonics comprising the Fourier series approximation 42.
Figure 2C:
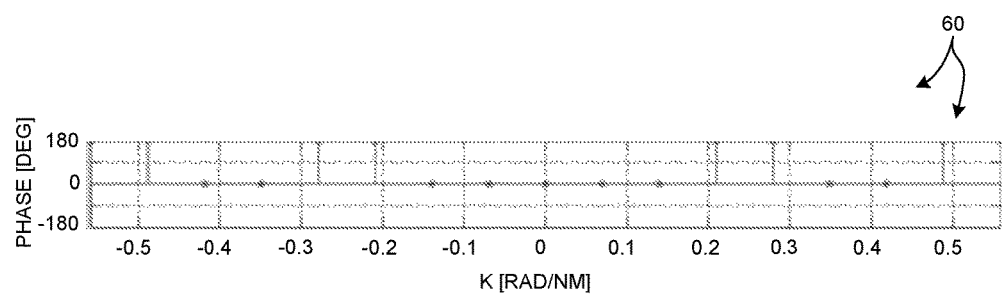
FIG. 2C depicts a plot 60 illustrative of the phase of the spatial harmonics comprising the Fourier series approximation 42.

FIG. 2A depicts a plot 40 illustrative of a periodic target function 41 also having a spatial period, P, in the x-direction. FIG. 2A also illustrates a Fourier series approximation 42 of the periodic target function 41. FIG. 2B depicts a plot 50 illustrative of the amplitude of the spatial harmonics comprising the Fourier series approximation up to the selected truncation order value, TO=40. Note that the spatial harmonics associated with the black, filled squares are used as part of the Fourier series approximation 42, while the spatial harmonics associated with the white, unfilled squares a not used as part of the Fourier series approximation 42. FIG. 2C depicts a plot 60 illustrative of the phase of the spatial harmonics comprising the Fourier series approximation up to the selected truncation order value.

Note that any multiple of the spatial period, P, is also a period of exactly the same function. In the example, depicted in FIGS. 2A-2C, the selected fundamental period of the Fourier series expansion is five times larger than the actual period, P'=5 P. In this example, the spacing between adjacent Fourier harmonics in k-space is 5 times smaller than the example described with reference to FIGS. 1A-1C. As depicted in FIG. 2B, the harmonic spacing in k-space is equal to $2\pi/5$ P. However, the periodic function 41 to be approximated is the same function as periodic function 11 described with reference to FIG. 1A. Thus, the Fourier series expansion of periodic function 41 must be essentially the same as the Fourier series expansion of periodic function 11. As depicted in FIG. 2B, this is achieved when the harmonics having an index multiple of five (i.e., 0, +/−5, +/−10, +/−15, etc.) are non-zero, while the remaining harmonics are zero valued.

It is important to note that if the selected fundamental period of the Fourier series expansion is a multiple of the underlying spatial period, a higher Truncation Order needs to be used to achieve a particular goodness of fit, compared to the scenario where the selected fundamental period of the Fourier series expansion matches the underlying spatial period. As illustrated in FIGS. 1A-1C, a particular goodness of fit was achieved with a truncation order of eight. However, to achieve the same goodness of fit in the example illustrated in FIGS. 2A-2C, a truncation order of forty is required. The increase in truncation order is exactly by the same factor as the ratio of the different selected fundamental periods of the Fourier series expansion. In the example depicted in FIGS. 2A-2C, the selected fundamental period of the Fourier series expansion (e.g., 5 P) is five times the selected fundamental period of the Fourier series expansion for the example depicted in FIGS. 1A-1C (e.g., P). Hence, a truncation order five times larger (e.g., TO=40) is required in the example depicted in FIGS. 2A-2C to achieve the same result.

These examples illustrate that when the selected fundamental period of the Fourier series expansion is a multiple of the actual spatial period of any function being approximated, the computational effort increases dramatically. Computational effort typically scales with the cube of the TO and memory requirements typically scale with the square of the TO for a two dimensional structure. Computational effort typically scales with the sixth power of the TO and memory requirements typically scale with the fourth power of the TO for a three dimensional structure. Thus, in this example, a 5× increase in TO results in approximately a 125× (i.e., $5^3$) increase in computational effort.

Figures 3, 4:
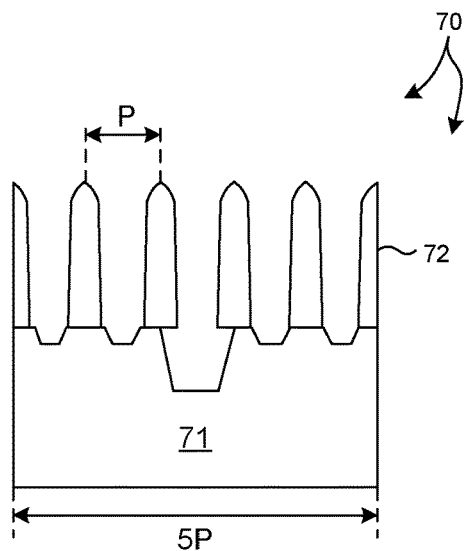
FIG. 3 depicts a structure 70 having two stacked gratings, each with different spatial periods.
FIG. 4 depicts a table 80 illustrating the increase in computational effort associated with various ratios of multiple periods.

FIG. 3 depicts a structure 70 having two stacked gratings, each with different spatial periods. Grating 72 having a pitch, P, is located on top of grating 71 having a pitch, 5 P. Structure 70 is a periodic target having multiple periods including a large fundamental spatial period, and an additional period that is an integer fraction (i.e., 1:5) of the large fundamental spatial period.

To approximate the periodic structure 70, the fundamental period of the Fourier series expansion should match the large fundamental spatial period, 5 P. However, as described hereinbefore, this results in a small harmonic spacing (i.e., $2\pi/5$ P) and relatively large truncation order to accurately approximate grating 72 to the same degree of accuracy as grating 71, simultaneously. As described hereinbefore, an increase in truncation order of 5× is required, and this results in approximately a 125× increase in computational effort. In many examples, this increase in computational effort is impractical, and users are forced to reduce the TO and sacrifice accuracy.

FIG. 4 depicts a table 80 illustrating the increase in computational effort associated with various ratios of multiple periods. As illustrated, if the ratio of large-to-small periods is higher than 1:5, the increase in computational effort becomes extreme. However, even with a ratio of 2:1, the increase in computational effort is 8×.

As illustrated in FIG. 4, the increase in computational effort associated with measurements of targets exhibiting multiple periodicity quickly becomes untenable if all of the spatial harmonic orders within the range of the truncation order are computed. In some examples, a sparse truncation order sampling pattern is employed to reduce computational effort. The methods described in U.S. Patent Publication No. 2011/0288822 A1 by Veldman et al. and U.S. Pat. No. 7,428,060 B2 to Jin et al., are used to automatically select sparse truncation order sampling patterns, essentially be trial and error. However, the number of patterns tested by these techniques can become very large for complex, multiple periodic structures. The number of patterns may be as large as a few hundred in a two-dimensional example, and as large as a few tens of thousands in a three-dimensional example. An exhaustive search of these patterns can be impractical.

In one aspect, the selection of Fourier spatial harmonics is based on the multiple periodicity of the metrology target. The Fourier spatial harmonics associated with each distinct period of the target are grouped separately. A distinct truncation order and a distinct spacing between selected harmonics are selected for each group. This approach produces optimal, sparse truncation order sampling patterns, and ensures that only harmonics with significant contributions to the approximation of the target are selected for computation. Furthermore, the computational effort associated with grouping and selecting harmonics in the manner described herein is minimal compared to existing approaches.

The selected harmonics are subsequently used for regression, library generation, or other analyses where simulated model based measurement signals are typically employed as part of an effort to characterize structural, material, and process parameters in semiconductor manufacturing.

Selecting harmonics in the manner described herein significantly reduces the computational effort associated with EM solvers that utilize Fourier expansions, including regression, library generation, and other analyses. Furthermore, previously impractical measurement models of large pitch and complex three dimensional structures are solved with reasonable computational effort. In some measurement applications, real-time regression is enabled and measurement accuracy is improved.

The techniques described herein are applicable to targets with multiple periodicities. Targets with multiple periodicities are becoming more prolific with the development of multiple patterning techniques, fin cutting techniques, the fabrication of complex three dimensional FinFETs arranged into groups, etc. In one example, targets having multiple periodicities are generated by a process where an initially produced grating with a small period is later divided by a "Fin Cutting" process into groups of fins with a larger overall period. Exemplary multiple patterning processes include Self Aligned Double Patterning (SADP) and Self-Aligned Quadruple Patterning (SAQP), Self-Aligned Octuple Patterning (SAOP), etc. However, in general, the methods and system described herein may be applied to the measurement of targets generated by any multiple patterning technique.

Targets with multiple periodicity are also becoming more common with the development of more complex structures. In some examples, structures having stacked, multiple gratings, each with a different period, are fabricated.

The techniques described herein apply when a metrology target has a fundamental spatial period that truly repeats as viewed from the perspective of the metrology system and one or more, smaller periods that are approximate, underlying the fundamental period. The smaller periods are integer fractions of the fundamental period of the structure. In one example, a metrology target may include two periodic structures of unequal pitch, for example, 11 nanometers and 29 nanometers. Together they form a fundamental periodic pattern with a period of 319 nanometers (i.e., 29*11=319). In the traditional approach, the TO would be dictated by the largest period (e.g., 319). However, employing the methods and systems described herein, multiple, smaller TOs can be selected, resulting in a tremendous reduction in computational effort. In this example, this metrology target includes a fundamental period at 319 nanometers and two approximate periods at 11 nanometers and 29 nanometers. Each of these approximate periods is an integer fraction of the fundamental.

The techniques described herein are applicable to EM algorithms that include truncated spatial harmonic series. In some examples, the EM algorithm is entirely based on truncated spatial harmonic series. Examples include RCWA, classical modal method, Fourier-based finite difference method, etc. In some other examples, the EM algorithm is a mixed or hybrid EM algorithm which at least one algorithmic component is based on truncated spatial harmonic series. Examples include, mixed RCWA-finite element solvers, mixed Finite Difference Time Domain and RCWA solvers, mixed Finite Difference Frequency Domain and RCWA solvers, etc. These non-limiting examples are provided for illustrative purposes, and application of the techniques described herein is not limited to the algorithms listed. In general, the techniques described herein may be applied to any number of different EM algorithms that include truncated spatial harmonic series as an element of the algorithm.

In general, multiple periodicities are manifest in one or more directions. For example, the techniques described herein are applicable to the analysis of two-dimensional targets with multiple periods aligned in one direction in space. In some other examples, the techniques described herein are applicable to the analysis of three-dimensional targets with multiple periods aligned in one direction in space, and one or more periods aligned in another direction. Typically the second direction is orthogonal to the first direction, however, in some examples, the two directions are not orthogonal.

Figure 5:
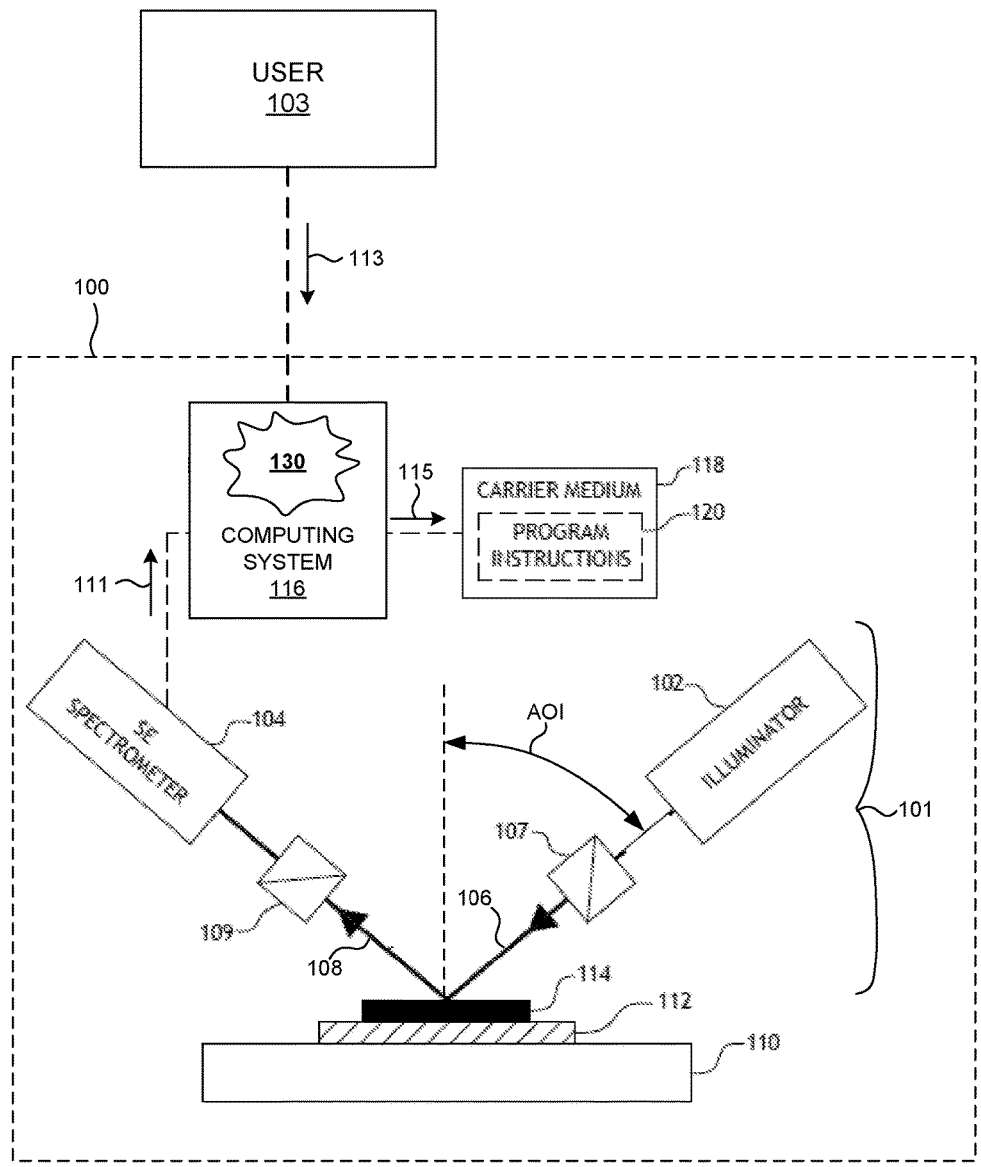
FIG. 5 illustrates a system 100 for measuring characteristics of a semiconductor wafer.

FIG. 5 illustrates a system 100 for measuring characteristics of a semiconductor wafer. As shown in FIG. 5, the system 100 may be used to perform spectroscopic ellipsometry measurements of one or more structures 114 of a semiconductor wafer 112 disposed on a wafer positioning system 110. In this aspect, the system 100 may include a spectroscopic ellipsometer 101 equipped with an illuminator 102 and a spectrometer 104. The illuminator 102 of the system 100 is configured to generate and direct illumination of a selected wavelength range (e.g., 150-1700 nm) to the structure 114 disposed on the surface of the semiconductor wafer 112. In turn, the spectrometer 104 is configured to receive light from the surface of the semiconductor wafer 112. It is further noted that the light emerging from the illuminator 102 is polarized using a polarization state generator 107 to produce a polarized illumination beam 106. The radiation reflected by the structure 114 disposed on the wafer 112 is passed through a polarization state analyzer 109 and to the spectrometer 104. The radiation received by the spectrometer 104 in the collection beam 108 is analyzed with regard to polarization state, allowing for spectral analysis of radiation passed by the analyzer. These spectra 111 are passed to the computing system 116 for analysis of the structure 114.

In a further embodiment, metrology system 100 includes one or more computing systems 116 configured to execute model truncation tool 130 including truncation of multiple groups of spatial harmonics functionality in accordance with the description provided herein. In the preferred embodiment, the model truncation tool 130 is a set of program instructions 120 stored on a carrier medium 118. The program instructions 120 stored on the carrier medium 118 are read and executed by computing system 116 to realize model based measurement functionality as described herein. The one or more computing systems 116 may be communicatively coupled to the spectrometer 104. In one aspect, the one or more computing systems 116 are configured to receive measurement data 111 associated with a measurement (e.g., critical dimension, film thickness, composition, process, etc.) of the structure 114 of specimen 112. In one example, the measurement data 111 includes an indication of the measured spectral response of the specimen by measurement system 100 based on the one or more sampling processes from the spectrometer 104. In some embodiments, the one or more computing systems 116 are further configured to determine specimen parameter values of structure 114 from measurement data 111. In one example, the one or more computing systems 116 are configured to access model parameters in real-time, employing Real Time Critical Dimensioning (RTCD), or it may access libraries of pre-computed models for determining a value of at least one specimen parameter value associated with the target structure 114.

In addition, in some embodiments, the one or more computing systems 116 are further configured to receive user input 113 from a user 103 such as model geometry, etc. The one or more computer systems are further configured to truncate multiple groups of spatial harmonics as described herein.

In some embodiments, measurement system 100 is further configured to store estimated parameter values 115 in a memory (e.g., carrier medium 118).

It should be recognized that the various steps described throughout the present disclosure may be carried out by a single computer system 116 or, alternatively, a multiple computer system 116. Moreover, different subsystems of the system 100, such as the spectroscopic ellipsometer 101, may include a computer system suitable for carrying out at least a portion of the steps described herein. Therefore, the aforementioned description should not be interpreted as a limitation on the present invention but merely an illustration. Further, the one or more computing systems 116 may be configured to perform any other step(s) of any of the method embodiments described herein.

The computing system 116 may include, but is not limited to, a personal computer system, mainframe computer system, workstation, image computer, parallel processor, or any other device known in the art. In general, the term "computing system" may be broadly defined to encompass any device having one or more processors, which execute instructions from a memory medium. In general, computing system 116 may be integrated with a measurement system such as measurement system 100, or alternatively, may be separate from any measurement system. In this sense, computing system 116 may be remotely located and receive measurement data and user input 113 from any measurement source and input source, respectively.

Program instructions 120 implementing methods such as those described herein may be transmitted over or stored on carrier medium 118. The carrier medium may be a transmission medium such as a wire, cable, or wireless transmission link. The carrier medium may also include a computer-readable medium such as a read-only memory, a random access memory, a magnetic or optical disk, or a magnetic tape.

In addition, the computer system 116 may be communicatively coupled to the spectrometer 104 or the illuminator subsystem 102 of the ellipsometer 101, or the user input source 103 in any manner known in the art.

The computing system 116 may be configured to receive and/or acquire data or information from the user input source 103 and subsystems of the system (e.g., spectrometer 104, illuminator 102, and the like) by a transmission medium that may include wireline and/or wireless portions. In this manner, the transmission medium may serve as a data link between the computer system 116, user input source 103, and other subsystems of the system 100. Further, the computing system 116 may be configured to receive measurement data via a storage medium (i.e., memory). For instance, the spectral results obtained using a spectrometer of ellipsometer 101 may be stored in a permanent or semi-permanent memory device (not shown). In this regard, the spectral results may be imported from an external system. Moreover, the computer system 116 may send data to external systems via a transmission medium.

The embodiments of the system 100 illustrated in FIG. 5 may be further configured as described herein. In addition, the system 100 may be configured to perform any other block(s) of any of the method embodiment(s) described herein.

Figure 6:
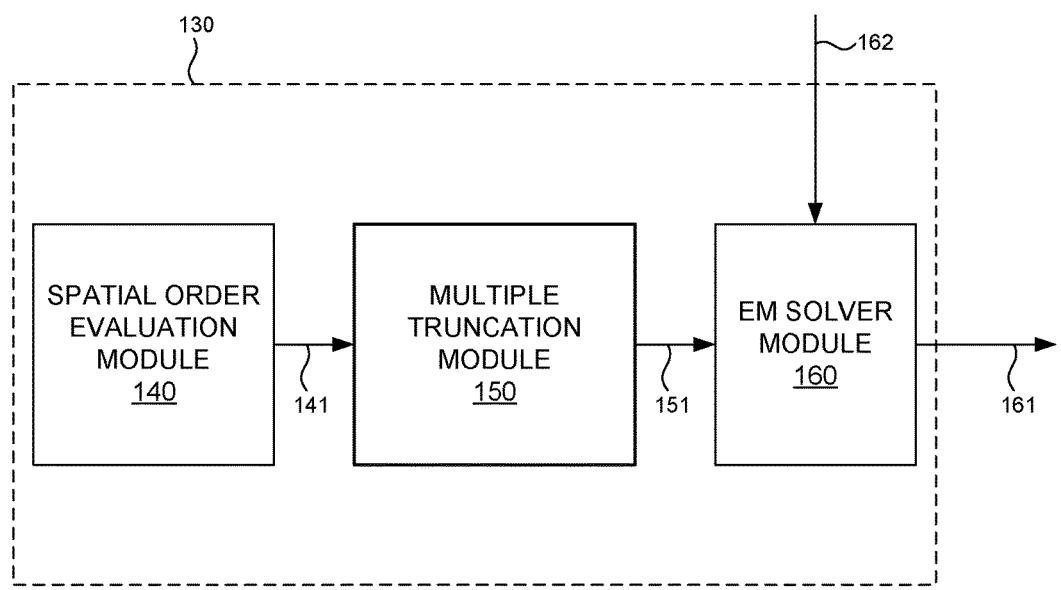
FIG. 6 depicts a model truncation tool 130 in one embodiment.

FIG. 6 depicts model truncation tool 130 in one embodiment. As depicted in FIG. 6, model truncation tool 130 includes a spatial order evaluation module 140, multiple truncation module 150, and EM Solver module 160.

Figure 7:
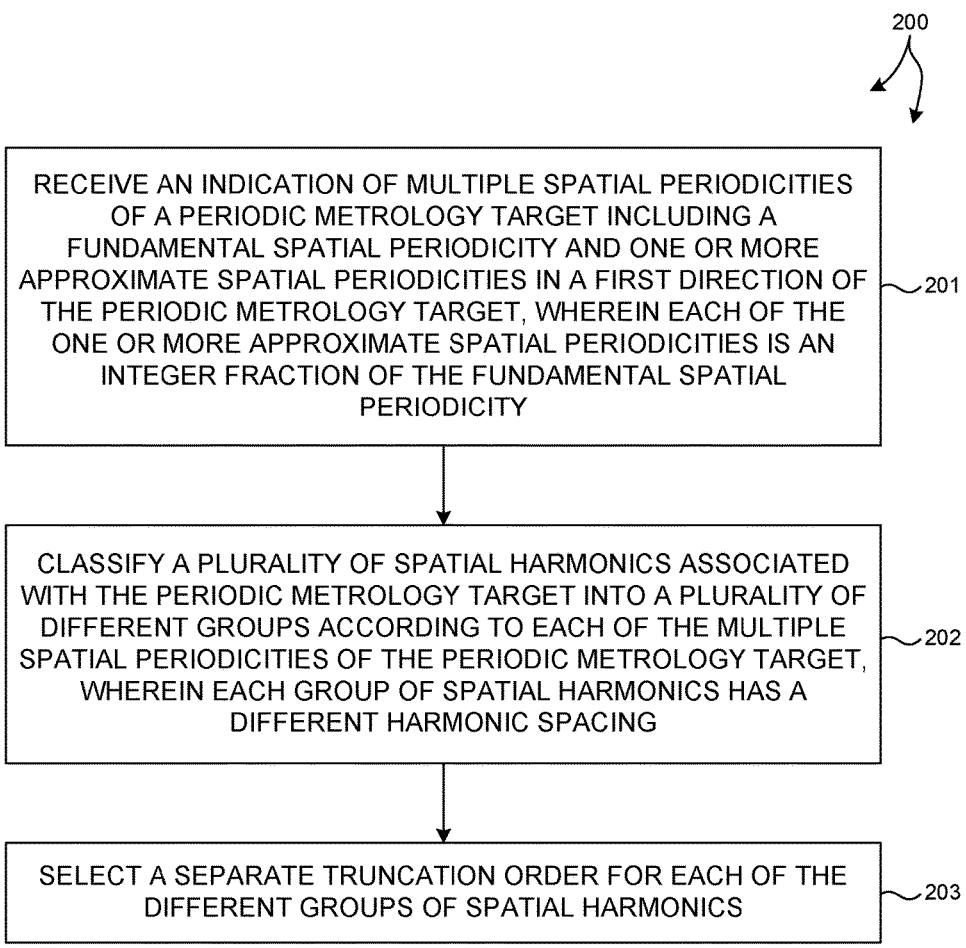
FIG. 7 illustrates a method 200 suitable for implementation by model truncation tool 130 illustrated in FIG. 6 of the present invention.

FIG. 7 illustrates a method 200 suitable for implementation by model truncation tool 130 illustrated in FIG. 6 of the present invention. In one aspect, it is recognized that data processing blocks of method 200 may be carried out via a pre-programmed algorithm executed by one or more processors of computing system 116, or any other general purpose computing system. It is recognized herein that the particular structural aspects of model truncation tool 130 do not represent limitations and should be interpreted as illustrative only.

In block 201, an indication of each period of the metrology target is received by spatial evaluation module 140. In some examples, multiple periods are input by a user based on prior knowledge of the multiple periods of the target to be computed. In these examples, user input 113 includes an indication of the periods of the metrology target. In some other examples, a user interacts with metrology software to create a geometric model of the metrology target. The metrology software generates an indication of the periods of the metrology target (e.g., graphics database system (GDSII) files) and communicates the indication to spatial evaluation module 140.

In some other examples, spatial evaluation module 140 receives an indication of the geometry of the metrology target (e.g., GDSII file) and computes the Fourier series of the dielectric permittivity of the target geometry up to a relatively high truncation order. Spatial evaluation module 140 then searches for multiple periods (one fundamental and one or more quasi-periods) by analyzing the amplitudes of the harmonics and classifying them into groups based on their rate of decay. These computations involve a simple Fourier transform of the dielectric permittivity function and analysis of the harmonics. These computations require very little computational effort, in comparison to a full EM simulation.

In some examples, spatial evaluation module 140 receives an indication of the geometry of the metrology target and determines each of the multiple periods by an analysis of the target geometry itself.

In some other examples, spatial evaluation module 140 determines an indication of each period of the metrology target based on a combination of user input (e.g., indications of possible periods) and an algorithm to detect actual periods that generate distinct groups of Fourier harmonics.

Figure 10A:
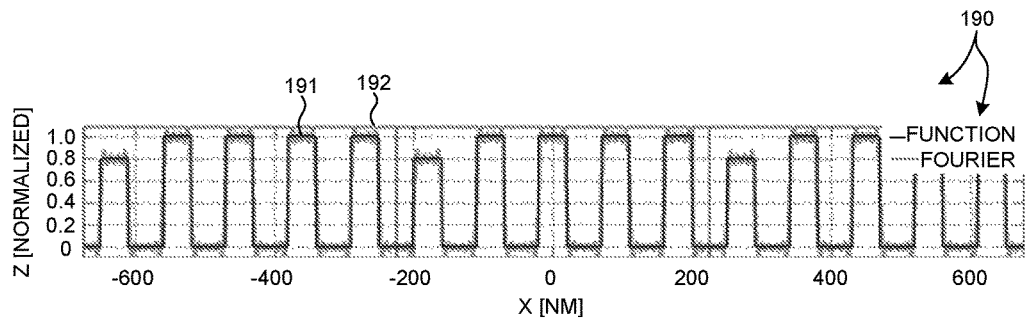
FIG. 10A depicts a plot 190 illustrative of a multiple periodic target function 191 and a Fourier series approximation 192 of the periodic target function 191.
Figure 10B:
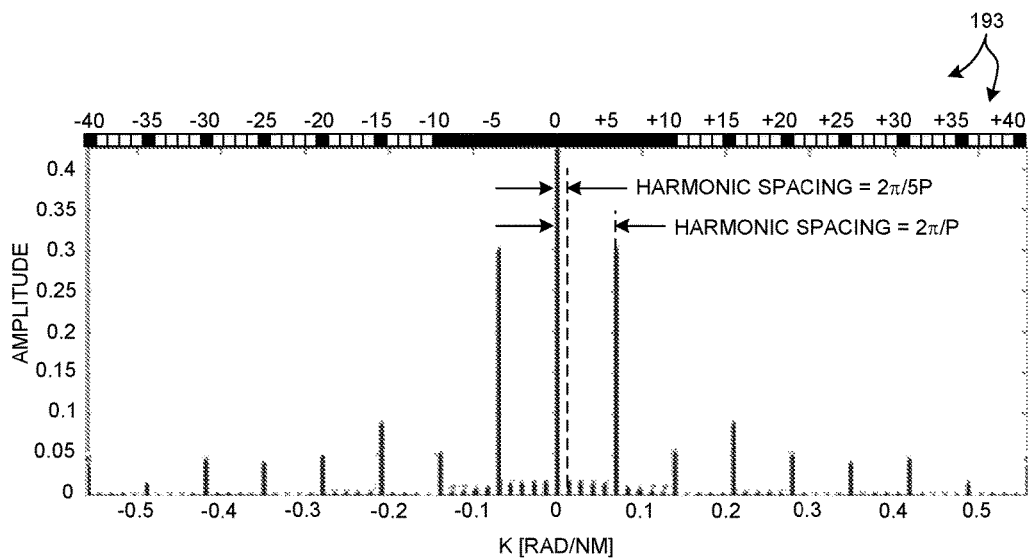
FIG. 10B depicts a plot 193 illustrative of the amplitude of the spatial harmonics comprising the Fourier series approximation 192.
Figure 10C:
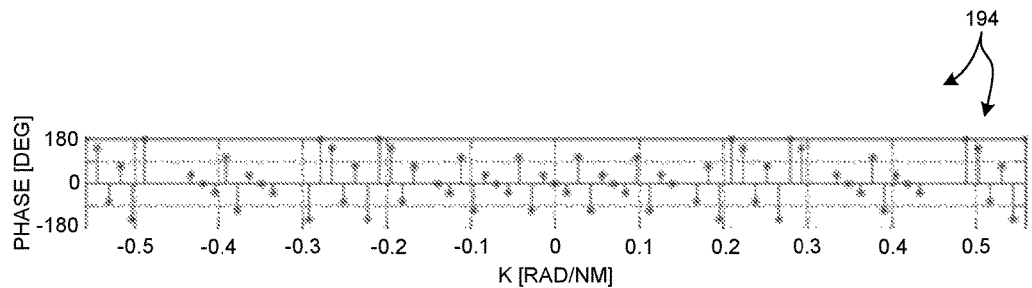
FIG. 10C depicts a plot 194 illustrative of the phase of the spatial harmonics comprising the Fourier series approximation 192.
Figure 11A:
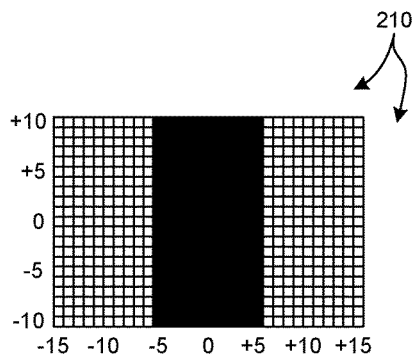
FIGS. 11A-11E illustrate a series of patterns of spatial harmonics associated with structure 70 depicted in FIG. 3.
Figure 11B:
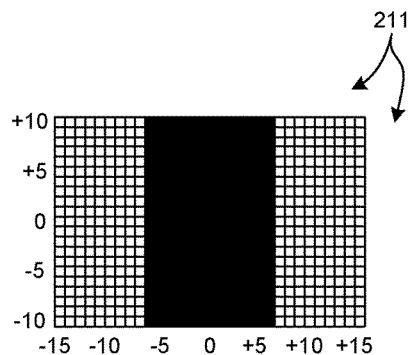
Figure 11C:
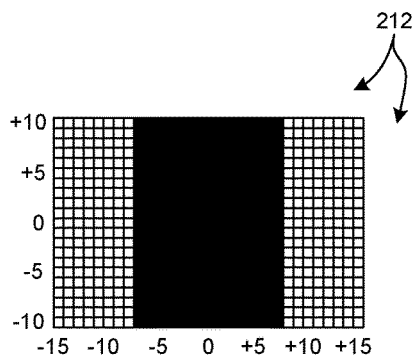
Figure 11D:
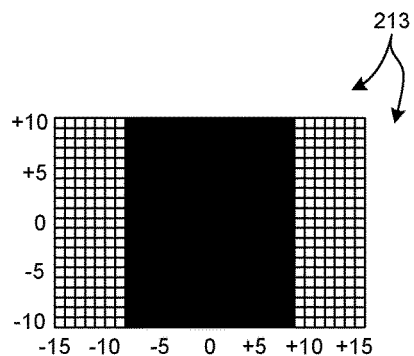
Figure 11E:
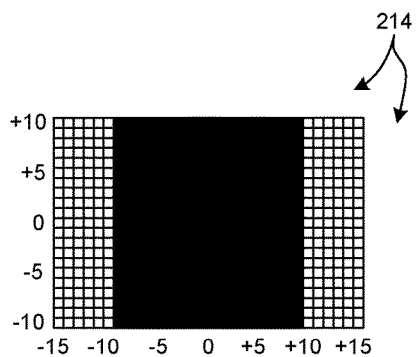
Figure 12A:
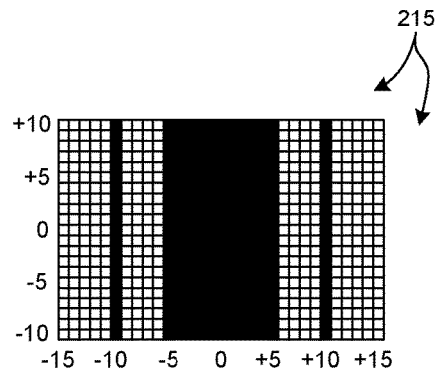
FIGS. 12A-12E illustrate another series of patterns of spatial harmonics associated with structure 70 depicted in FIG. 3.
Figure 12B:
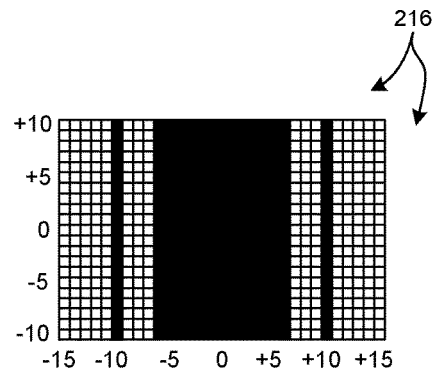
Figure 12C:
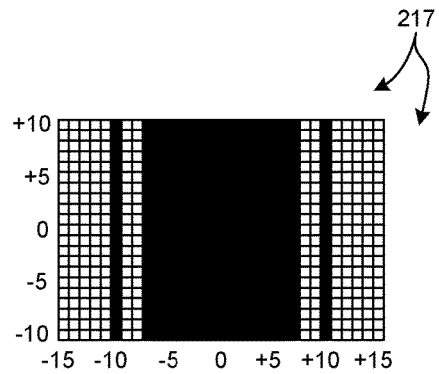
Figure 12D:
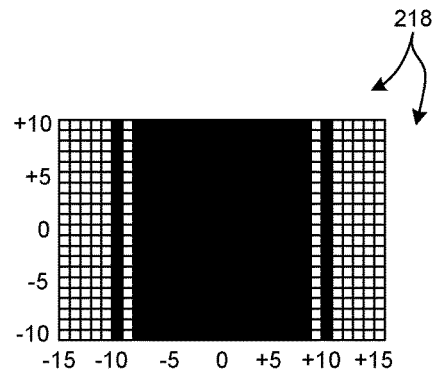
Figure 12E:
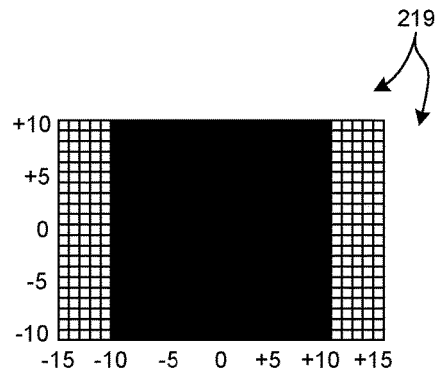
Figure 13A:
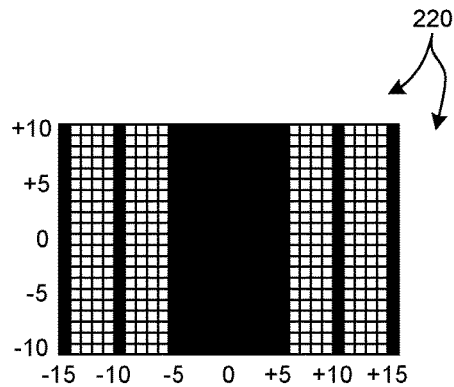
FIGS. 13A-13I illustrate another series of patterns of spatial harmonics associated with structure 70 depicted in FIG. 3.
Figure 13B:
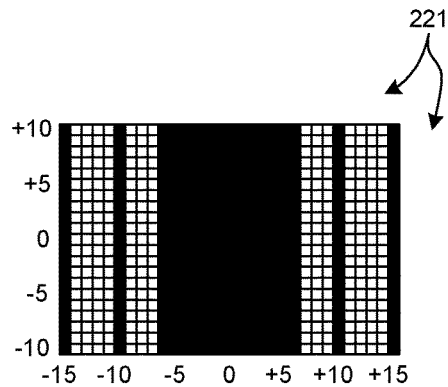
Figure 13C:
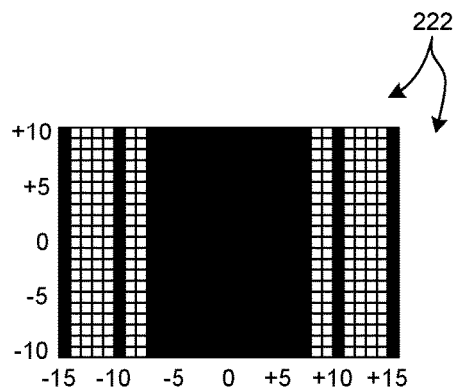
Figure 13D:
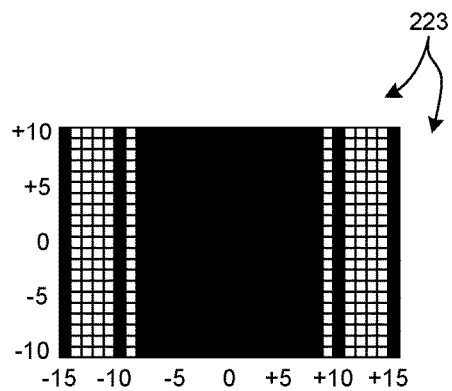
Figure 13E:
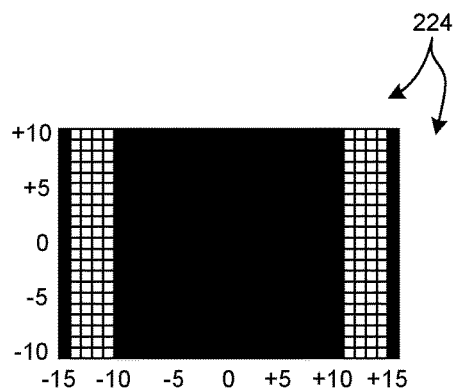
Figure 13F:
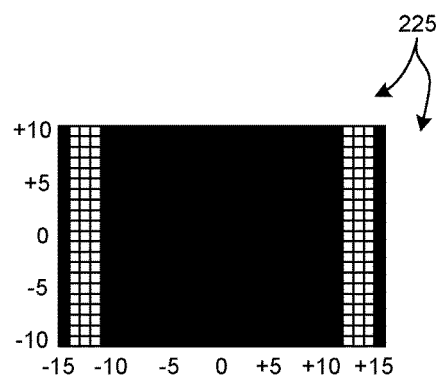
Figure 13G:
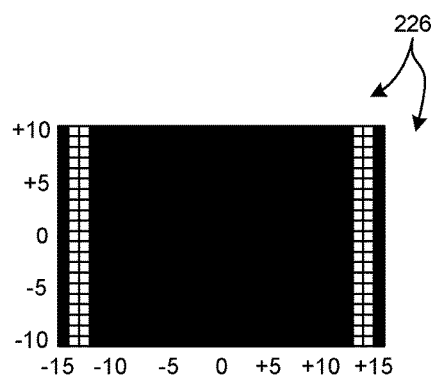
Figure 13H:
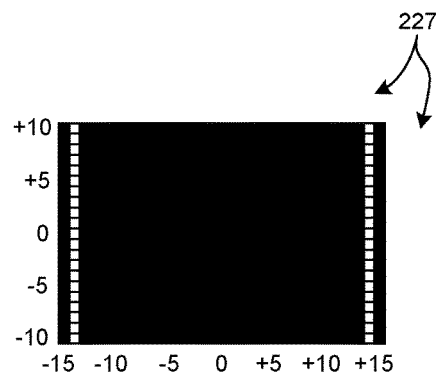
Figure 13I:
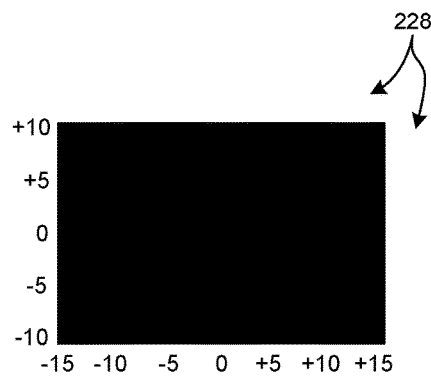

In block 202, spatial order evaluation module 140 classifies the spatial harmonics into different groups according to each period of the metrology target. An example of the classification of Fourier spatial harmonics into different groups based on multiple periods is depicted in FIGS. 10A-10C. FIG. 10A depicts a plot 190 illustrative of a multiple periodic target function 191 having a spatial period, P=90 nanometers, in the x-direction. In addition, there is a perturbation that appears every fifth period, at 5 P=450 nanometers. Thus, the fundamental period of the Fourier series expansion is 450 nanometers, and the smaller, approximate period is an integer fraction of the fundamental (i.e., 1:5). FIG. 2A also illustrates a Fourier series approximation 192 of the periodic target function 191. FIG. 10B depicts a plot 193 illustrative of the amplitude of the spatial harmonics comprising the Fourier series approximation up to the selected truncation order value, TO=40. Note that the spatial harmonics associated with the black, filled squares are used as part of the Fourier series approximation 192, while the spatial harmonics associated with the white, unfilled squares a not used as part of the Fourier series approximation 192. FIG. 10C depicts a plot 194 illustrative of the phase of the spatial harmonics comprising the Fourier series approximation up to the selected truncation order value.

As depicted in FIG. 10B, the Fourier spatial harmonics of the metrology target with double periodicity (e.g., structure 70 depicted in FIG. 3), fall into two distinct groups, with different rates of decay. Group 1 harmonics are associated with period, P, and have relatively large amplitude and large harmonic spacing, $2\pi/P$. The indices associated with the Group 1 harmonics are $\{0, +/-5, +/-10, +/-15, +/-20, +/-25, +/-30, +/-35, +/-40\}$. Group 2 harmonics are associated with period, 5 P, and have relatively small amplitude and large harmonic spacing, $2\pi/5$ P. The indices associated with the Group 2 harmonics are $\{+/-1, +/-2, +/-3, +/-4, +/-6, +/-7, +/-8, +/-9, +/-11, +/-12, +/-13, +/-14, \ldots\}$. In this manner, spatial harmonics associated with each spatial period are grouped together.

Spatial order evaluation module 140 communicates each group of spatial harmonics 141 to multiple truncation module 150.

In block 203, multiple truncation module 150 selects a separate truncation order for each group of harmonics and communicates the selected truncation orders to EM solver module 160. In this manner, the non-compact set of harmonics includes multiple groups of harmonics, each having their own period, truncation order, and k-space spacing. In the example illustrated in FIGS. 10A-10C, a truncation order of nine is applied to the Group 2 harmonics. In addition, a truncation order of forty is applied to the Group 1 harmonics, however, for Group 1 harmonics, only harmonics whose index is a multiple of five are used for further analysis. Thus, the effective number of selected harmonics for Group 1 is eight, rather than forty.

As depicted in FIG. 10B, there is a striking difference in the decay rate of the two groups of harmonics. The Group 1 harmonics decay slowly and retain significant amplitude at very high values of their index, but are widely spaced. The Group 2 harmonics decay much faster and are tightly spaced. In some embodiments, the truncation order associated with each of the plurality of different groups of spatial harmonics is selected by first determining an amplitude of each of the spatial harmonics of each of the plurality of different groups, for example as depicted in FIG. 10B. Furthermore, the truncation order associated with each of the plurality of different groups is selected based on a rate of decay of the amplitude of the spatial harmonics of each of the plurality of different groups. In this manner, a higher TO is selected for slowly decaying groups of harmonics and a lower TO is selected for quickly decaying groups of harmonics.

In a preferred embodiment, the selection of the truncation order associated with each of the plurality of different groups of spatial harmonics involves performing a separate convergence test for each of the plurality of different groups of spatial harmonics using an electromagnetic simulator that utilizes a Fourier expansion of the periodic metrology target in terms of the plurality of spatial harmonics.

In a further aspect, the classification of spatial harmonics into groups with separate truncation orders is implemented in each direction of the metrology target that exhibits multiple periodicity.

Figure 8:
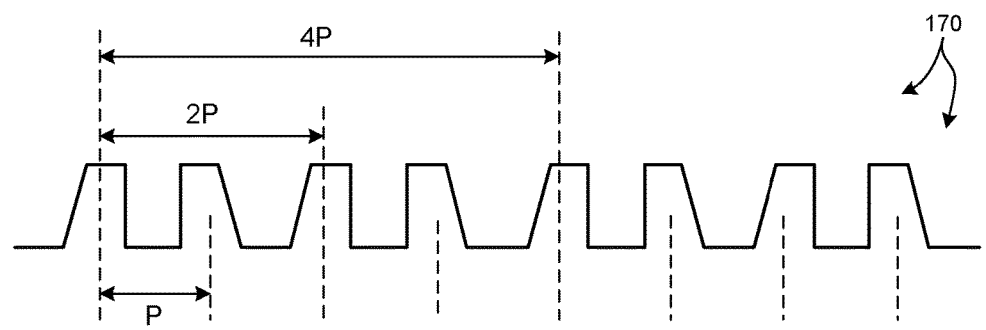
FIG. 8 depicts a cross-sectional view of a metrology target 170 that is periodic in one direction with triple periodicity.

FIG. 8 depicts a cross-sectional view of a metrology target 170 that is periodic in one direction with triple periodicity. As depicted in FIG. 8, metrology target 170 is fabricated by a Self-aligned Quadruple Patterning process, and exhibits a large, fundamental period, 4 P, and two smaller, approximate periods, 2 P, and P. In this example, three groups of spatial harmonics are identified and a separate truncation order is assigned to each group of harmonics.

Figure 9:
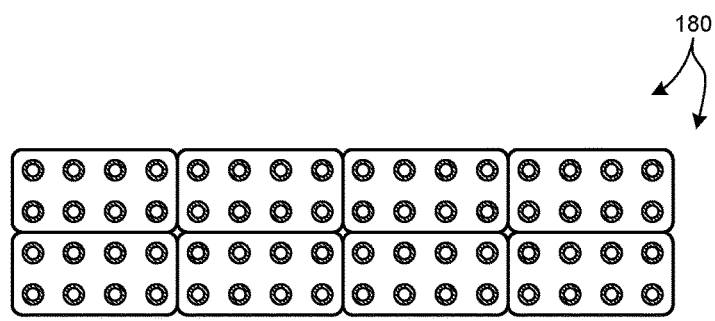
FIG. 9 depicts a top-down view of a three dimensional metrology target 180 that exhibits double periodicity in two orthogonal directions.

FIG. 9 depicts a top-down view of a three dimensional metrology target 180 that exhibits double periodicity in two orthogonal directions, (e.g., x-direction and y-direction). In this example, there is a double period in the x-direction with a period ratio of 1:4. In addition, there is a double period in the y-direction with a period ration of 1:2. By grouping spatial harmonics into two groups in both the x and y directions, and assigning separate truncation orders each group of harmonics, a very significant reduction in computational effort for a given accuracy target is achieved.

In a further aspect, EM solver module 160 receives measured signals 162. In some embodiments, measured signals 162 are detected by a spectroscopic measurement system (e.g., spectrometer 104 depicted in FIG. 5) configured to perform spectroscopic measurements of a specimen (e.g., structure 114).

In another further aspect, EM solver module 160 performs a regression analysis to estimate one or more parameters of interest of the specimen based on a fitting of the measurement model truncated in accordance with truncation orders 151 to the measured signals 162.

Although the methods discussed herein are explained with reference to system 100, any model based optical metrology system configured to illuminate and detect light reflected, transmitted, or diffracted from a specimen may be employed to implement the exemplary methods described herein. Exemplary systems include an angle-resolved reflectometer, a scatterometer, a reflectometer, an ellipsometer, a spectroscopic reflectometer or ellipsometer, a beam profile reflectometer, a multi-wavelength, two-dimensional beam profile reflectometer, a multi-wavelength, two-dimensional beam profile ellipsometer, a rotating compensator spectroscopic ellipsometer, etc. By way of non-limiting example, an ellipsometer may include a single rotating compensator, multiple rotating compensators, a rotating polarizer, a rotating analyzer, a modulating element, multiple modulating elements, or no modulating element.

It is noted that the output from a source and/or target measurement system may be configured in such a way that the measurement system uses more than one technology. In fact, an application may be configured to employ any combination of available metrology sub-systems within a single tool, or across a number of different tools.

A system implementing the methods described herein may also be configured in a number of different ways. For example, a wide range of wavelengths (including visible, ultraviolet, infrared, and X-ray), angles of incidence, states of polarization, and states of coherence may be contemplated. In another example, the system may include any of a number of different light sources (e.g., a directly coupled light source, a laser-sustained plasma light source, etc.). In another example, the system may include elements to condition light directed to or collected from the specimen (e.g., apodizers, filters, etc.).

FIGS. 11-13 illustrate a series of patterns of spatial harmonics associated with structure 70 depicted in FIG. 3. As depicted in FIG. 3, structure 70 includes two periodic grating structures with a 5:1 multiple periodicity. Note that the spatial harmonics associated with the black, filled squares are used as part of the Fourier series approximation, while the spatial harmonics associated with the white, unfilled squares a not used as part of the Fourier series approximation.

The metrology target is three dimensional. Different patterns of spatial harmonics associated with the x-direction are explored. A fixed truncation order of 10 is selected for the y-direction.

Patterns 210-214 depicted in FIGS. 11A-11E employ a single truncation order and each spatial harmonic less than the selected truncation order is considered as part of the approximation for structure 70. Pattern 210 includes a single truncation order of five. Pattern 211 includes a single truncation order of six. Pattern 212 includes a single truncation order of seven. Pattern 213 includes a single truncation order of eight. Pattern 214 includes a single truncation order of nine.

Patterns 215-219 depicted in FIGS. 12A-12E employ two truncation orders as described herein. Each truncation order is associated with a different group of spatial harmonics of the Fourier approximation of structure 70. Pattern 215 includes a truncation order value of five applied to the group of spatial harmonics associated with large pitch structure 71, having harmonic spacing of $2\pi/5$ P. Pattern 215 also includes a truncation order value of ten applied to the group of spatial harmonics associated with small pitch structure 72, having harmonic spacing of $2\pi/P$. However, only harmonics whose index is a multiple of five are used as part of the Fourier approximation. Thus, the effective number of selected harmonics for the group of spatial harmonics associated with small pitch structure 72 is two, rather than ten. Pattern 216 is the same as pattern 215, except that a truncation order value of six is applied to the group of spatial harmonics associated with large pitch structure 71. Pattern 217 is the same as pattern 215, except that a truncation order value of seven is applied to the group of spatial harmonics associated with large pitch structure 71. Pattern 218 is the same as pattern 215, except that a truncation order value of eight is applied to the group of spatial harmonics associated with large pitch structure 71. Pattern 219 is the same as pattern 215, except that a truncation order value of nine is applied to the group of spatial harmonics associated with large pitch structure 71. Note that pattern 219 is a compact pattern, in the sense that the pattern selection is the same as if a single truncation order of ten was selected across all spatial harmonics.

Patterns 220-228 depicted in FIGS. 13A-13I employ two truncation orders as described herein. As described hereinbefore, each truncation order is associated with a different group of spatial harmonics of the Fourier approximation of structure 70. Pattern 220 includes a truncation order value of five applied to the group of spatial harmonics associated with large pitch structure 71, having harmonic spacing of $2\pi/5$ P. Pattern 220 also includes a truncation order value of fifteen applied to the group of spatial harmonics associated with small pitch structure 72, having harmonic spacing of $2\pi/P$. However, only harmonics whose index is a multiple of five are used as part of the Fourier approximation. Thus, the effective number of selected harmonics for the group of spatial harmonics associated with small pitch structure 72 is three, rather than fifteen. Patterns 221-224 are the same as pattern 220, except that a truncation order value of six, seven, eight, and nine, respectively, is applied to the group of spatial harmonics associated with large pitch structure 71. Similarly, patterns 225-228 are the same as pattern 220, except that a truncation order value of eleven, twelve, thirteen, and fourteen, respectively, is applied to the group of spatial harmonics associated with large pitch structure 71. Note that pattern 228 is a compact pattern, in the sense that the pattern selection is the same as if a single truncation order of fifteen was selected across all spatial harmonics.

Figure 14:
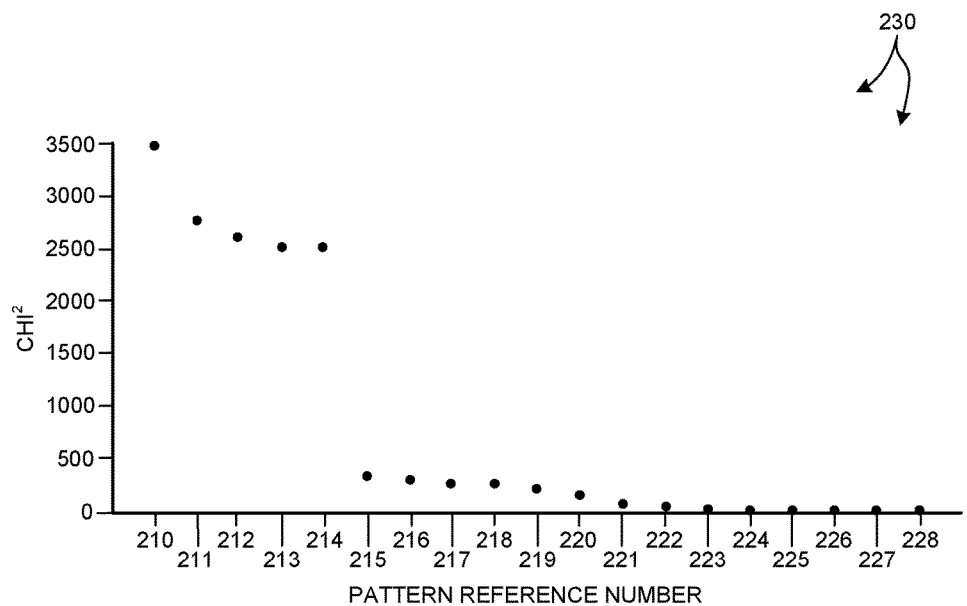
FIG. 14 depicts a plot 230 illustrative of a goodness of fit between results predicted by RCWA computations using Fourier approximations of structure 70 truncated in accordance with each of the patterns 210-228, compared with the result obtained from pattern 228.
Figure 15:
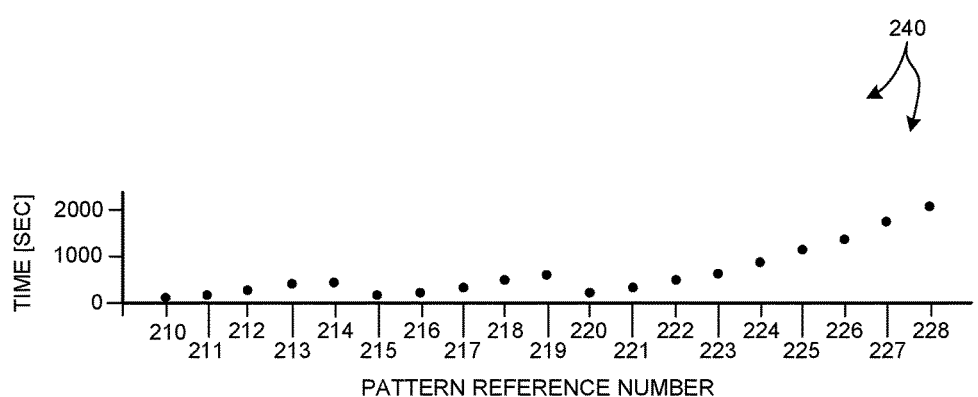
FIG. 15 depicts a plot 240 illustrative of the computation time associated with each of the RCWA simulations depicted in FIG. 14.

FIG. 14 depicts a plot 230 illustrative of the goodness of fit (measured as a chi-squared value) between results predicted by RCWA computations using Fourier approximations of structure 70 truncated in accordance with each of the patterns 210-228, compared with the result obtained from pattern 228. FIG. 15 depicts a plot 240 illustrative of the computation time associated with each of the RCWA simulations depicted in FIG. 14. It is noted that the computational effort associated with pattern 219 used in a three dimensional computation is close to the limit of practical use in a semiconductor manufacturing environment. Thus, computational efforts greater than pattern 219 are impractical.

The results depicted in FIG. 14 and FIG. 15 illustrate that increasing a single truncation order applied across all spatial harmonics produces only modest increases in accuracy, but at increasing computational cost. This is visible in patterns 210-214, 219, and 228. However, by introducing two different truncation orders, each applied to different groups of spatial harmonics, a dramatic increase in accuracy is achieved, along with a reduction in computational effort. This is visible in patterns 215-218. In addition, pattern 220 exhibits improved accuracy over pattern 219 and significantly less computational effort.

For metrology targets having multiple periodicities, the methods and systems described herein enable both higher accuracy and reduced computational effort compared to existing approaches.

In a further aspect, the methods and systems described herein are applied to EM algorithms that approximate finite target effects by assuming a periodic target with a small period divided into patches having a much larger period. In this manner a finite target is analyzed by dividing the target grating into periodic patches.

Figure 16:
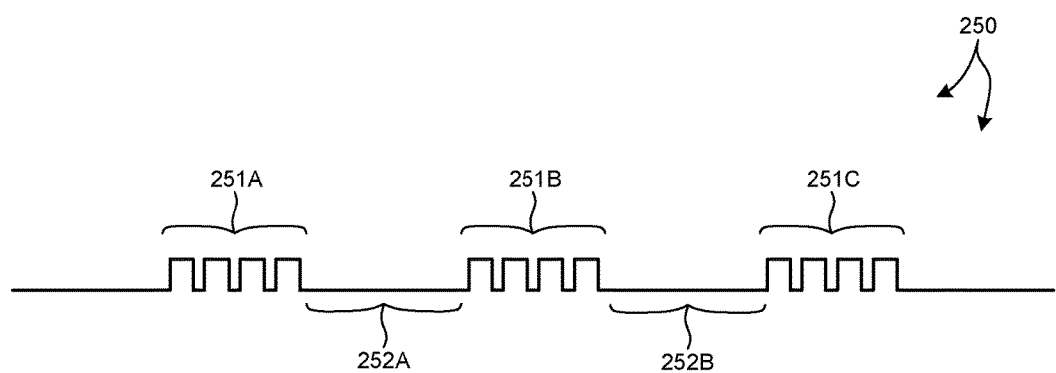
FIG. 16 depicts a cross-section of a double-period structure 250, which can be used to compute metrology targets that are finite in size.

FIG. 16 depicts a cross-section of a proposed double-period structure 250, which can be used to compute metrology targets which are finite in size by using a period much larger than the basic period of the target grating. Such an approximation of a finite-size target may use a different model for the portions of the structure 252A-B that surround the measurement patches 251A-C. Such a model may be another grating, a simple film stack, or a strongly absorbing or non-reflecting material.

In some examples, the non-compact pattern of harmonics derived from multiple periods as described herein is used directly in an electromagnetic computation. In some examples, the electromagnetic computations are employed for critical dimension metrology, critical dimension target optimization, etc. In some other examples, the electromagnetic computations are employed for scatterometry overlay metrology, scatterometry overlay target design, etc. In some other examples, the electromagnetic computations are employed for imaging overlay metrology and for imaging overlay target design. Such methods are described in further detail in U.S. Pat. No. 8,214,771 to Michael Adel, et al., the contents of which are incorporated herein by reference in its entirety.

In some other examples, the electromagnetic computations are employed with a secondary target in optical CD metrology, overlay metrology, and optimization of the secondary target. Further details are described in U.S. Patent Publication No. 2013/0116978 by Yoo et al., the contents of which are incorporated herein by reference in their entirety.

In some other examples, the electromagnetic computations are employed with multiple targets in optical CD metrology, overlay metrology, and optimization of multiple targets. Further details are described in U.S. Pat. No. 7,478,019 to Zangooie et al., the contents of which are incorporated herein by reference in their entirety.

In some other examples, the electromagnetic computations are employed as part of edge placement error metrology, CD metrology, overlay metrology, or any combination thereof.

In some other examples, the electromagnetic computations are employed in the analysis of device-like targets located in the scribe line, on-device targets located within the die, or a combination thereof.

In some other examples, the non-compact pattern is used in a truncation convergence test.

As described herein, the term "critical dimension" includes any critical dimension of a structure (e.g., bottom critical dimension, middle critical dimension, top critical dimension, sidewall angle, grating height, etc.), a critical dimension between any two or more structures (e.g., distance between two structures), a displacement between two or more structures (e.g., overlay displacement between overlaying grating structures, etc.), and a dispersion property value of a material used in the structure or part of the structure. Structures may include three dimensional structures, patterned structures, overlay structures, etc.

As described herein, the term "critical dimension application" or "critical dimension measurement application" includes any critical dimension measurement.

As described herein, the term "metrology system" includes any system employed at least in part to characterize a specimen in any aspect. However, such terms of art do not limit the scope of the term "metrology system" as described herein. In addition, the metrology system 100 may be configured for measurement of patterned wafers and/or unpatterned wafers. The metrology system may be configured as a LED inspection tool, edge inspection tool, backside inspection tool, macro-inspection tool, or multi-mode inspection tool (involving data from one or more platforms simultaneously), and any other metrology or inspection tool that benefits from the multiple truncation of different groups of spatial harmonic orders as described herein.

Various embodiments are described herein for a semiconductor processing system (e.g., an inspection system or a lithography system) that may be used for processing a specimen. For example, an indication of an estimated value of one or more parameters of interest is transmitted to a fabrication cluster (e.g., a semiconductor fabrication tool) configured to perform a processing step. The estimated value of one or more parameters of interest is used to adjust one or more parameters of the fabrication process (i.e., modify a process variable or equipment setting for the processing step performed by the fabrication cluster). The term "specimen" is used herein to refer to a site, or sites, on a wafer, a reticle, or any other sample that may be processed (e.g., printed or inspected for defects) by means known in the art. In some examples, the specimen includes a single site having one or more measurement targets whose simultaneous, combined measurement is treated as a single specimen measurement or reference measurement. In some other examples, the specimen is an aggregation of sites where the measurement data associated with the aggregated measurement site is a statistical aggregation of data associated with each of the multiple sites. Moreover, each of these multiple sites may include one or more measurement targets associated with a specimen or reference measurement.

As used herein, the term "wafer" generally refers to substrates formed of a semiconductor or non-semiconductor material. Examples include, but are not limited to, monocrystalline silicon, gallium arsenide, and indium phosphide. Such substrates may be commonly found and/or processed in semiconductor fabrication facilities. In some cases, a wafer may include only the substrate (i.e., bare wafer). Alternatively, a wafer may include one or more layers of different materials formed upon a substrate. One or more layers formed on a wafer may be "patterned" or "unpatterned." For example, a wafer may include a plurality of dies having repeatable pattern features.

A "reticle" may be a reticle at any stage of a reticle fabrication process, or a completed reticle that may or may not be released for use in a semiconductor fabrication facility. A reticle, or a "mask," is generally defined as a substantially transparent substrate having substantially opaque regions formed thereon and configured in a pattern. The substrate may include, for example, a glass material such as amorphous $SiO_2$. A reticle may be disposed above a resist-covered wafer during an exposure step of a lithography process such that the pattern on the reticle may be transferred to the resist.

One or more layers formed on a wafer may be patterned or unpatterned. For example, a wafer may include a plurality of dies, each having repeatable pattern features. Formation and processing of such layers of material may ultimately result in completed devices. Many different types of devices may be formed on a wafer, and the term wafer as used herein is intended to encompass a wafer on which any type of device known in the art is being fabricated.

In one or more exemplary embodiments, the functions described may be implemented in hardware, software, firmware, or any combination thereof. If implemented in software, the functions may be stored on or transmitted over as one or more instructions or code on a computer-readable medium. Computer-readable media includes both computer storage media and communication media including any medium that facilitates transfer of a computer program from one place to another. A storage media may be any available media that can be accessed by a general purpose or special purpose computer. By way of example, and not limitation, such computer-readable media can comprise RAM, ROM, EEPROM, CD-ROM or other optical disk storage, magnetic disk storage or other magnetic storage devices, or any other medium that can be used to carry or store desired program code means in the form of instructions or data structures and that can be accessed by a general-purpose or special-purpose computer, or a general-purpose or special-purpose processor. Also, any connection is properly termed a computer-readable medium. For example, if the software is transmitted from a website, server, or other remote source using a coaxial cable, fiber optic cable, twisted pair, digital subscriber line (DSL), or wireless technologies such as infrared, radio, and microwave, then the coaxial cable, fiber optic cable, twisted pair, DSL, or wireless technologies such as infrared, radio, and microwave are included in the definition of medium. Disk and disc, as used herein, includes compact disc (CD), laser disc, optical disc, digital versatile disc (DVD), floppy disk and blu-ray disc where disks usually reproduce data magnetically, while discs reproduce data optically with lasers. Combinations of the above should also be included within the scope of computer-readable media.

Although certain specific embodiments are described above for instructional purposes, the teachings of this patent document have general applicability and are not limited to the specific embodiments described above. Accordingly, various modifications, adaptations, and combinations of various features of the described embodiments can be practiced without departing from the scope of the invention as set forth in the claims.

What is claimed is:

1. A measurement system comprising:
an illumination source configured to provide an amount of illumination light to a periodic metrology target having multiple spatial periods including a fundamental spatial period and one or more approximate spatial periods in a first direction of the periodic metrology target, wherein each of the one or more approximate spatial periods is an integer fraction of the fundamental spatial period;
a detector configured to receive an amount of collected light from the periodic metrology target in response to the amount of illumination light and generate a plurality of measured signals; and
one or more computing systems configured to:
receive an indication of the multiple spatial periods of the periodic metrology target;
classify a plurality of spatial harmonics associated with the periodic metrology target into a plurality of different groups according to each of the multiple spatial periods of the periodic metrology target, wherein each group of spatial harmonics has a different harmonic spacing;
select a truncation order associated with each of the plurality of different groups of spatial harmonics;
estimate a value of one or more parameters of interest of the periodic metrology target based on a fitting of a measurement model, simulated at the selected truncation orders, to the measured signals; and
communicate an indication of the value of the one or more parameters of interest to a semiconductor fabrication tool that causes the semiconductor fabrication tool to adjust one or more parameters of a fabrication process of the semiconductor fabrication tool.

2. The measurement system of claim 1, wherein the measurement model, simulated at the selected truncation orders, includes an electromagnetic simulator utilizing a Fourier expansion of the periodic metrology target in terms of the plurality of spatial harmonics.

3. The measurement system of claim 1, wherein the indication of the multiple spatial periods of the metrology target is received from a user.

4. The measurement system of claim 1, further comprising:
determining each of the multiple spatial periods of the periodic metrology target.

5. The measurement system of claim 4, wherein the determining of each of the multiple spatial periods of the periodic metrology target involves:
computing a Fourier series of spatial harmonics of a dielectric permittivity of the periodic metrology target geometry to a relatively high truncation order; and
analyzing the amplitudes of each of the spatial harmonics of the Fourier series.

6. The measurement system of claim 4, wherein the determining of each of the multiple spatial periods of the periodic metrology target involves an analysis of the geometry of the periodic etrology target.

7. The measurement system of claim 1, wherein the selecting of the truncation order associated with each of the plurality of different groups of spatial harmonics involves:
determining an amplitude of each of the spatial harmonics of each of the plurality of different groups; and
selecting the truncation order associated with each of the plurality of different groups based on a rate of decay of the amplitude of the spatial harmonics of each of the plurality of different groups.

8. The measurement system of claim 1, wherein the selecting of the truncation order associated with each of the plurality of different groups of spatial harmonics involves:
performing a separate convergence test for each of the plurality of different groups of spatial harmonics using an electromagnetic simulator that utilizes a Fourier expansion of the periodic metrology target in terms of the plurality of spatial harmonics.

9. The measurement system of claim 1, wherein the periodic metrology target having multiple spatial periods in the first direction of the target, also includes multiple spatial periods in a second direction, different from the first direction, wherein the multiple spatial periods in the second direction includes a fundamental spatial period and one or more approximate spatial periods in the second direction of the periodic metrology target, wherein each of the one or more approximate spatial periods in the second direction is an integer fraction of the fundamental spatial period in the second direction.

10. The measurement system of claim 1, wherein a different truncation order is associated with each of the plurality of different groups of spatial harmonics.

11. The measurement system of claim 2, wherein the electromagnetic simulator is a Fourier based electromagnetic simulator.

12. The measurement system of claim 1, wherein the periodic metrology target includes a first periodic target having a relatively small pitch divided into groups by a second periodic pattern having a relatively large pitch.

13. The measurement system of claim 2, wherein the parameters of interest include any of a critical dimension parameter and an overlay parameter.

14. A method for improving electromagnetic computation efficiency in optical metrology, the method comprising:
providing an amount of illumination light from an illumination source of a semiconductor measurement system to a periodic metrology target having multiple spatial periods including a fundamental spatial period and one or more approximate spatial periods in a first direction of the periodic metrology target, wherein each of the one or more approximate spatial periods is an integer fraction of the fundamental spatial period;
receiving an amount of collected light onto a detector of the semiconductor measurement system from the periodic metrology target in response to the amount of illumination light and generating a plurality of measured signals;
receiving an indication of multiple spatial periods of a periodic metrology target including a fundamental spatial period and one or more approximate spatial periods in a first direction of the periodic metrology target, wherein each of the one or more approximate spatial periods is an integer fraction of the fundamental spatial period;
classifying a plurality of spatial harmonics associated with the periodic metrology target into a plurality of different groups according to each of the multiple spatial periods of the periodic metrology target, wherein each group of spatial harmonics has a different harmonic spacing;
selecting a separate truncation order for each of the different groups of spatial harmonics;
estimating a value of one or more parameters of interest of the periodic metrology target based on a fitting of a measurement model, simulated at the selected truncation orders, to the measured signals; and communicating an indication of the value of the one or more parameters of interest to a semiconductor fabrication tool that causes the semiconductor fabrication tool to adjust one or more parameters of a fabrication process of the semiconductor fabrication tool.

15. The method of claim 14, wherein the measurement model simulated at the selected truncation orders includes an electromagnetic simulator utilizing a Fourier expansion of the periodic metrology target in terms of the plurality of spatial harmonics.

16. The method of claim 14, further comprising:
determining each of multiple spatial periods of the metrology target, wherein the determining involves:
computing a Fourier series of spatial harmonics of a dielectric permittivity of the periodic metrology target geometry to a relatively high truncation order; and
analyzing the amplitudes of each of the spatial harmonics.

17. The method of claim 14, wherein the selecting of the separate truncation order associated with each of the plurality of different groups of spatial harmonics involves:
performing a separate convergence test for each of the plurality of different groups of spatial harmonics using an electromagnetic simulator that utilizes a Fourier expansion of the periodic metrology target in terms of the plurality of spatial harmonics.

18. A measurement system comprising:
an illumination source configured to provide an amount of illumination light to a periodic metrology target having multiple spatial periods including a fundamental spatial period and one or more approximate spatial periods in a first direction of the periodic metrology target, wherein each of the one or more approximate spatial periods is an integer fraction of the fundamental spatial period;
a detector configured to receive an amount of collected light from the periodic metrology target in response to the amount of illumination light and generate a plurality of measured signals; and
a non-transitory, computer-readable medium, comprising:
code for causing a computing system to receive an indication of multiple spatial periods of a periodic metrology target including a fundamental spatial period and one or more approximate spatial periods in a first direction of the periodic metrology target, wherein each of the one or more approximate spatial periods is an integer fraction of the fundamental spatial period;
code for causing the computing system to classify a plurality of spatial harmonics associated with the periodic metrology target into a plurality of different groups according to each of the multiple spatial periods of the periodic metrology target, wherein each group of spatial harmonics has a different harmonic spacing;
code for causing the computing system to select a separate truncation order for each of the different groups of spatial harmonics
code for causing the computing system to estimate a value of one or more parameters of interest of the periodic metrology target based on a fitting of a measurement model, simulated at the selected truncation orders, to the measured signals; and
code for causing the computing system to communicate an indication of the value of the one or more parameters of interest to a semiconductor fabrication tool that causes the semiconductor fabrication tool to adjust one or more parameters of a fabrication process of the semiconductor fabrication tool.

19. The measurement system of claim 18, wherein the measurement model simulated at the selected truncation orders includes an electromagnetic simulator utilizing a Fourier expansion of the periodic metrology target in terms of the plurality of spatial harmonics.

20. The measurement system of claim 18, wherein the selecting of the truncation order associated with each of the plurality of different groups of spatial harmonics involves:
performing a separate convergence test for each of the plurality of different groups of spatial harmonics using an electromagnetic simulator that utilizes a Fourier expansion of the periodic metrology target in terms of the plurality of spatial harmonics.

* * * * *